United States Patent
De Quadros, Jr. et al.

(10) Patent No.: US 9,303,140 B2
(45) Date of Patent: *Apr. 5, 2016

(54) PRIMARY PVC PLASTICIZERS DERIVED FROM VEGETABLE OILS, PROCESS FOR OBTAINING PRIMARY PVC PLASTICIZERS DERIVED FROM VEGETABLE OILS AND PLASTICIZED PVC COMPOSITION

(71) Applicant: Nexoleum Bioderivados Ltda., Cotia, Sao Paulo (BR)

(72) Inventors: Jacyr Vianna De Quadros, Jr., Sao Paulo (BR); Jose Augusto De Carvalho, Sao Paulo (BR)

(73) Assignee: Nexoleum Bioderivados Ltda, De Sao Paulo (BR)

( * ) Notice: Subject to any disclaimer, the term of this patent is extended or adjusted under 35 U.S.C. 154(b) by 234 days.

This patent is subject to a terminal disclaimer.

(21) Appl. No.: 14/148,312

(22) Filed: Jan. 6, 2014

(65) Prior Publication Data

US 2014/0221538 A1  Aug. 7, 2014

Related U.S. Application Data

(63) Continuation-in-part of application No. 12/331,068, filed on Dec. 9, 2008, now Pat. No. 8,623,947.

(30) Foreign Application Priority Data

Dec. 10, 2007  (BR) ...................................... 0705621

(51) Int. Cl.
*C08K 5/1515* (2006.01)
*C08K 5/04* (2006.01)
*C08K 5/00* (2006.01)

(52) U.S. Cl.
CPC ................. *C08K 5/04* (2013.01); *C08K 5/0016* (2013.01); *C08K 5/1515* (2013.01)

(58) Field of Classification Search
CPC ........ C08L 27/06; C08K 5/04; C08K 5/1515; C08K 5/0016
USPC .................................. 524/114, 313, 317, 318
See application file for complete search history.

(56) References Cited

U.S. PATENT DOCUMENTS

| | | | | | |
|---|---|---|---|---|---|
| 2,822,368 | A | * | 2/1958 | Rowland | C08K 5/1515 524/109 |
| 3,281,382 | A | * | 10/1966 | Kuester | C08K 5/1515 524/114 |
| 3,377,304 | A | * | 4/1968 | Kuester | C08K 5/101 524/114 |
| 7,071,343 | B2 | * | 7/2006 | Daute | C11C 3/10 549/514 |
| 2012/0181056 | A1 | * | 7/2012 | Chaudhary | C07C 69/33 174/110 SR |

* cited by examiner

*Primary Examiner* — Wenwen Cai
(74) *Attorney, Agent, or Firm* — Kilpatrick Townsend & Stockton LLP

(57) ABSTRACT

PVC plasticizers are composed of epoxidized bioesters of vegetable oil fatty acids obtained by partial transesterification with an alcohol, and glycerin and further acetylation and epoxidation, and PVC compounds plasticized with bioesters resulting from partial transesterification, acetylation and epoxidation, belonging to the technical field of polymer additives that were developed to improve the properties of PVC polymers, in addition to providing a lower cost for renewable compounds, such as those obtained with the use of vegetable oils. The epoxidized bioesters are composed by mixtures of epoxidized ethyl esters and acetylated and epoxidized mono, di and triglyceril esters, presenting oxirane index equal to or less than 8.

2 Claims, No Drawings

PRIMARY PVC PLASTICIZERS DERIVED FROM VEGETABLE OILS, PROCESS FOR OBTAINING PRIMARY PVC PLASTICIZERS DERIVED FROM VEGETABLE OILS AND PLASTICIZED PVC COMPOSITION

CROSS-REFERENCES TO RELATED APPLICATIONS

This application is a continuation-in-part of U.S. patent application Ser. No. 12/331,068, filed Dec. 9, 2008, which is hereby incorporated by reference.

BACKGROUND OF THE INVENTION

The present descriptive report refers to a patent of invention of primary PVC plasticizers composed of epoxidized bioesters of vegetable oil fatty acids obtained by partial transesterification of vegetable oils with ethanol or glycerin and further acetylation and epoxidation, and plasticized PVC composition with epoxidized bioesters resulting from partial transesterification, acetylation and epoxidation, belonging to the technical field of polymer additives that were developed to improve the properties of PVC resin-based polymers, in addition to providing a lower cost for renewable compounds, such as those obtained with the use of vegetable oils.

Polyvinyl chloride (PVC) is a polymer well known for its wide range of industrial applications, but it presents natural rigidity due to its molecular structure, requiring the use of some additives to increase its range of useful applications, resulting in compositions that are commonly known as PVC compounds.

Among known compounds, plasticized PVC compounds present high flexibility and are used in films, wire and cable insulation, packaging, hoses, toys, etc. Plasticized PVC compounds are obtained by the addition, in different levels, of additives known as plasticizers, to provide the desired flexibility.

Plasticizers are, in general, high boiling point liquids with average molecular weight between 300 and 600, linear or cyclic carbon chains (14 to 40 carbons) that, when added to the PVC resin allow for movement between the PVC molecules promoting flexibility to the final compound.

Currently, primary plasticizers used in the industry are mainly phthalates, obtained from petroleum and, in addition to being dependent on the fluctuations of petroleum prices, phthalates are suspect of having adverse effects on human health.

As a result, a search was initiated to find alternatives that are technically and economically viable to replace petroleum based plasticizers. Epoxidized soybean oil was proposed as a primary plasticizer, however, its low compatibility with PVC limited its use to small quantities, keeping it from completely replacing phthalates as a primary plasticizer.

Another proposition was the use of epoxidized linseed oil, that in spite of having a similar molecular weight to soybean oil presents a higher oxirane index (8 to 12) and thus greater compatibility with PVC. However, its use is severely restricted due to its higher price.

As such, it was studied the processes of transesterification or interesterification of vegetable oils combined with epoxidation, as primary plasticizers for PVC. Patent GB934689 describes the preparation of vegetable oils with high linolenic acid contents (such as linseed oil), presenting high iodine index (175 to 200) and high oxirane index (8,5 to 12,33), that are transesterified with lower alcohols (methanol) and subsequently epoxidized. Patents U.S. Pat. Nos. 4,421,886 and 5,886,072 propose the use of esters of soybean oil transesterified with pentaeritritol, whereas the latter patent proposes the use of these esters in a mixture with other plasticizers. Patent U.S. Pat. No. 4,605,694 describes the use of trimelitic acid and pentaeritritol esters, while the patent U.S. Pat. No. 5,430,108 proposes the use of esters of pentaeritritol with alcanoic acid. Finally, the Brazilian patent application BR 0111905-2 describes the use of soybean oil transesterified with methanol, ethylene glycol, propylene glycol, pentaeritritol, saccharose, and interesterified linseed oil.

Some of these esters (obtained from pentaeritritol, trimelitic acid, ethylene glycol, propylene glycol and interesterified linseed oil) as plasticizers present the drawback of having larger molecular weight and much higher cost when compared to phthalates. Others obtained from methanol, still have a price dependency on petroleum. Additionally, the proposed esters are composed by mixtures of esters with oxirane indexes greater than 8. Finally, with exception of the methanol esters, the other types of esters have been used as primary plasticizers for PVC only in laboratory tests, indicating the difficulty in obtaining an additive that is both technically and economically viable.

Therefore, the objective of the present invention is to obtain technically and economically viable alternatives of primary plasticizers for PVC compounds derived exclusively from renewable sources (vegetable oils and sugar cane ethanol) that are completely compatible with the PVC resin.

With the purpose of overcoming the aforementioned problems and complying with the objectives previously described, the invention developed compositions of plasticizers obtained from the partial transesterification, acetylation and epoxidation of vegetable oils with ethanol or glycerin, henceforth called partially transesterified epoxidized bioesters. This invention differs from the state of the art by providing partially transesterified, acetylated and epoxidized bioester plasticizers composed of a mixture of mono, di and triglycerides and esters of vegetable oils fatty acids, presenting low linolenic acid content and oxirane indexes below 8.

Vegetable oils are composed by triglycerides that contain glycerin molecules attached to three saturated, monounsaturated, di-unsaturated and tri-unsaturated fatty acids such as palmitic, oleic, linoleic, and linolenic acids, among others. These fatty acids vary also in regards to the size of the carbon chain, presenting 14 to 18 carbon atoms for the oils referred in this invention.

The partial transesterification reaction of vegetable oils is employed to partly separate some of the fatty acids from the glycerin molecule and bond them to other alcohol molecules, resulting in a mixture of mono, di and triglycerides and esters of the partly transesterified vegetable oil. Such mixture presents superior properties when compared to those of the triglyceride. This wide range of ester varieties increases the possibilities of compatibility with PVC, in addition to allowing different properties in the plasticized PVC.

It is important to note that the current state of the art for the production of modified vegetable oils for PVC plasticizing as well as other applications, such as biodiesel, only mentions complete transesterification reactions, as partial reactions are not welcome and even detrimental to the production of such products as they are produced today.

The wide variety of bioesters obtained in the present invention increases the compatibility with the PVC resin, in addition to provide different properties to the plasticized PVC.

The partial transesterification reaction results mostly in the random substitution of the fatty acids of the vegetable oil molecule by one or two hydroxyl (OH) radicals, introducing one or two points of thermal instability in the resulting molecule. In order to correct for that and to provide the product with suitable chemical and physical characteristics to be used as a PVC plasticizer, the removal of such OH radicals is necessary.

Such elimination of the hydroxyl radical is carried through a process called acetylation, where the mono and diglyceride molecules are reacted with acetic acid, creating a short ramification with 2 carbon atoms. The acetylation reaction eliminates the OH radical in the molecules, and eliminates the thermal stability problem.

Finally, the epoxidation process introduces an atom of oxygen in the double bonds of the fatty acid carbon chains, forming an oxirane ring that makes the ester more polar and thus more compatible with the PVC resin. The greater the number of double bonds in the original ester, the greater the number of oxirane rings formed, and therefore increased compatibility with PVC. In addition, the substitution of the double bonds by the oxirane ring in the fatty acid chains increases the chemical and thermal stability of the resulting molecule.

The compatibility of the epoxidized bioesters with the PVC resin depends on the unsaturation of the original esters and the level of epoxidation of the double bonds. The bioesters of this invention present compatibility with PVC even when the resulting oxirane index is below 8, which is not foreseen in the current state of the art.

In a preferred embodiment the bioesters are obtained by the partial transesterification of a mixture of vegetable oils or one vegetable oil, such as soybean oil, with an alcohol in a smaller vegetable oil-to-alcohol ratio than the ratio used for a complete transesterification reaction. Alcohols used in the present invention may include aliphatic C1-C4 alcohols, such as methanol, ethanol, propanol, and butanol, as well as isomers thereof such as isopropanol, sec-butanol, isobutanol, and tert-butanol.

After obtained, the mixture of mono and diglycerides resulting from the partial reaction are acetylated with acetic acid to reduce or eliminate the hydroxyl radicals. The mixture of acetylated mono and diglycerides, as well as the triglycerides and esters of the vegetable oil fatty acids are then epoxidized. The vegetable oils are chosen among the oils with an iodine index between 120 and 170, such as soybean oil, corn oil, linseed oil, sunflower oil, or a mixture of them.

The plasticizer composition obtained by the partial transesterification of vegetable oils with ethanol, acetylation and epoxidation presents a mixture of the following molecules:

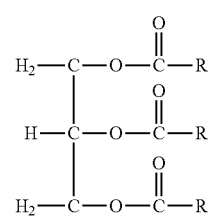

(I)

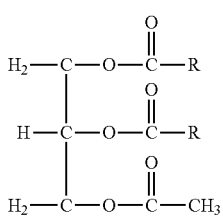

(II)

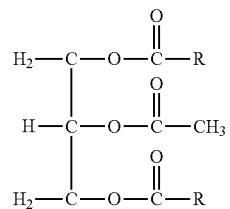

(III)

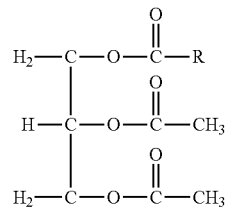

(IV)

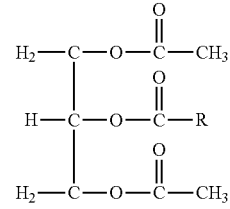

(V)

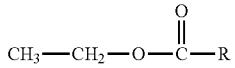

(VI)

With R preferably selected randomly from the epoxidized oleic, linoleic and linolenic acids.

The variation of reaction parameters such as catalyst amount, temperature, reaction time and oil: alcohol molar proportion allows for a wide range of possible compositions in the final mixture to obtain a product that best suits the desired application.

In a preferred embodiment the partial transesterification reaction is obtained by the use of 50% of the amount of catalyst for a complete reaction as well as a molar proportion of soybean oil: alcohol of 1:10 and 1:20. Alcohols that may be used include aliphatic C1-C4 alcohols, such as methanol, ethanol, propanol, and butanol, as well as isomers thereof such as isopropanol, sec-butanol, isobutanol, and tert-butanol. After obtained, the mono and diglycerides are reacted with acetic acid in the presence of pyridine to replace the hydroxyl radicals by acetic terminations. The mixture of acetylated mono and diglycerides and esters of the vegetable oil fatty acids are then epoxidized, in a reaction where the double bonds in the fatty acid chains react with in situ free oxygen obtained from high concentration peroxides, which under certain conditions of temperature and stirring form the oxirane rings. In this embodiment the product obtained had 10% of epoxidized triglycerides, 50% of epoxidized ethyl soyate and 40% of acetylated and epoxidized mono and diglycerides.

The final product obtained is a viscous transparent liquid slightly yellow and with a faint odor similar in characteristic to the original soybean oil used, presents an oxirane index between 4 and 8, long linear molecular chain (between 20 to 41 carbon atoms) and medium average molecular weight (between 450 and 500) when compared to the epoxidized soybean oil.

In another embodiment the plasticizers are obtained by the partial transesterification of a mixture of vegetable oils or one vegetable oil, such as soybean oil, with glycerin, under similar reaction conditions as those presented above. The vegetable oils are chosen among the oils with an iodine index between 120 and 170, such as soybean oil, corn oil, linseed oil, sunflower oil, or a mixture of them.

The composition of the plasticizer obtained by the partial transesterification of vegetable oils with glycerin and subsequent acetylation and epoxidation presents a mixture of the following molecules:

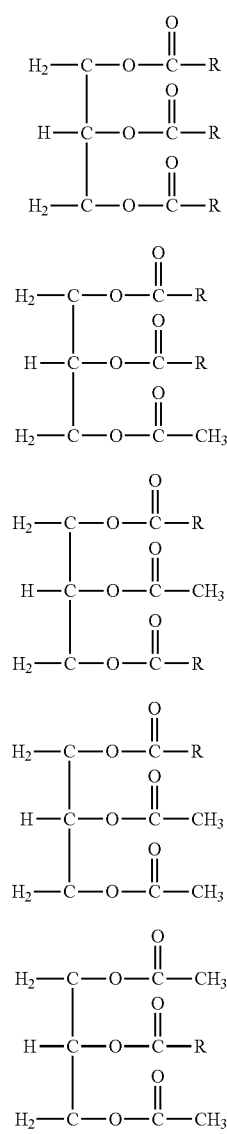

With R preferably selected randomly from the epoxidized oleic, linoleic and linolenic acids.

It is important to note that the glycerin used in this process is obtained from the very same reaction of complete transesterification of vegetable oils with alcohols and described in various processes, and therefore is also renewable.

In a preferred embodiment the soybean oil is reacted with pure glycerin in 1:0.2 to 1:0.4 soybean oil: glycerin proportions, at room pressure and temperatures between 170° C. e 220° C., using alkyl benzene sulfonate as catalyst, sodium ethylate or soda, resulting in a mixture of mono and triglycerides and at least 50% of diglycerides with fatty acid chains in the extremes of the glycerin molecule and the hydroxyl radical (OH) in the middle. This mixture is then acetylated and epoxidized according to the procedures indicated above.

Even though plasticizers obtained present acetylated epoxidized diglyceride of at least 50%. The final product obtained is a viscous transparent liquid slightly yellow and with a faint odor similar in characteristic to the original soybean oil used. Presenting an oxirane index between 4 and 8, long linear molecular chain with average 41 carbon atoms and medium to high average molecular weight (700) when compared to the epoxidized soybean oil (900).

In another embodiment, plasticized PVC is obtained by mixing i) 100 parts (weight/weight) of at least one type of PVC resin; ii) 1 to 200 parts (weight/weight) of plasticizer, which consists of epoxidized bioesters with an oxirane index below 8; the mixture is then homogenized and later extruded.

In a preferred embodiment the plasticizer is made from a fatty acid esters and glyceryl esters, derived from vegetable oil, partially transesterified with ethanol, which mono and diglycerides are acetylated and then, along the ethyl esters and triglycerides, are epoxidized. Such mixture is denominated epoxidized ethyl soyate and epoxidized mono, di and triglyceril soyates.

In another preferred embodiment the plasticizer is made from a mixture of partially transesterified mono, di and triglycerides of soybean oil acetylated and epoxidized, such mixture denominated epoxidized mono, di and triglyceril soyates, with at least 50% of epoxidized diglyceril soyate.

The plasticized PVC is therefore free of phthalate plasticizers. It is important to point out that the plasticizers composed of epoxidized bioesters of ethanol and/or epoxidized glycerides provide some property improvements to the plasticized PVC, improvements not foreseen in the state of the art, such as greater flexibility, greater resistance to UV light degradation, better physical properties at low temperatures, better mixture efficiency (solvation) of the PVC resin and better resistance to aliphatic solvents extraction.

PVC compounds plasticized with the objects of this invention present superiority in all these properties when compared to plasticized PVC prepared with plasticizers revealed by the state of the art while keeping the same proportion of plasticizer/PVC resin.

Therefore, the plasticizers of this invention work out the inconveniencies described in the state of the art, presenting the following additional advantages:

1. Can be produced from natural, renewable and economically viable sources (sugar cane and soybean oil), in addition to being adequate to human contact;
2. Are totally compatible with the PVC resin, when compared to the epoxidized soybean oil;
3. Present less odor and coloration when compared to the epoxidized soybean oil;
4. Present competitive costs when compared to all primary plasticizers and significantly lower costs when compared to the current alternatives to replace phthalates (trimelitates, citrates, polymerics) and lower costs when compared to most of the alternatives present in the state of the art, which use more expensive alcohols or acids;
5. Provide better solvation and plasticization efficiency in the PVC compound when compared to the current primary plasticizers alternatives or the majority of the developments of the state of the art, producing lighter and more flexible compounds with less plasticizers;

6. Aid in the thermal stabilization of PVC, allowing more processing tolerance or cost reduction of the stabilizers package, when compared to the current alternatives of primary plasticizers;

7. Offer better UV resistance to the PVC compound allowing the use of PVC compounds for longer periods or cost reduction of the UV protection additive packages, when compared to the current primary plasticizers alternatives;

8. Provide better physical properties at low temperatures, when compared to the current primary plasticizers alternatives based on phthalates;

9. Provide better resistance to aliphatic solvent extraction, when compared to current alternatives of primary plasticizers, mainly phthalates;

In summary, the objects of this invention present complementary benefits and additional advantages that are not foreseen by the state of the art.

The scope of this patent of invention shall not be limited to the described applications, but to the terms defined in the claims and its equivalents.

What is claimed is:

1. A plasticized polyvinyl chloride composition comprising:
    100 parts by weight of at least one polyvinyl chloride resin; and
    1 to 200 parts by weight of a primary plasticizer, which consists of a vegetable oil, an alcohol, acetic acid, and a compound of each of formulas (I) to (VI):

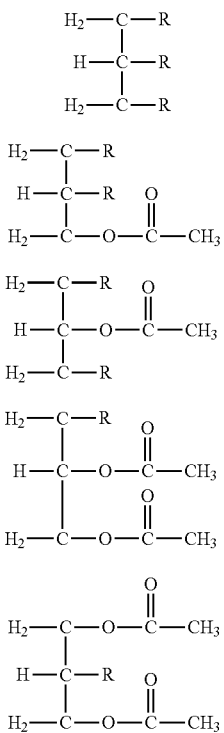

wherein R is independently an epoxidized oleyloxy group, an epoxidized linoleoyloxy group, or an epoxidized linolenoyloxy group; and wherein the primary plasticizer has an oxirane index of between 4 and 8.

2. A plasticized polyvinyl chloride composition comprising:
    100 parts by weight of at least one polyvinyl chloride resin; and
    1 to 200 parts by weight of a primary plasticizer, which consists of a vegetable oil, an alcohol, acetic acid, and a compound of each of formulas (I) to (VI):
wherein R is independently an epoxidized hydrocarbon chain having between 20 to 41 carbon atoms; and wherein the primary plasticizer has an oxirane index of between 4 and 8

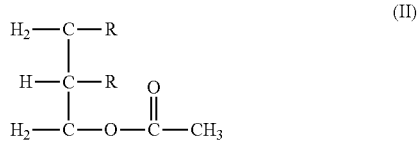

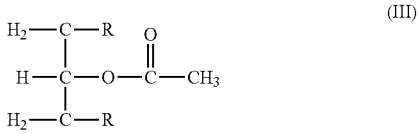

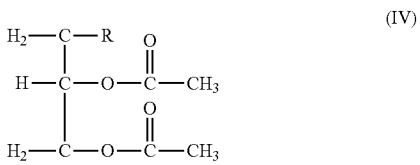

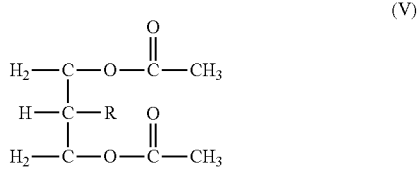

* * * * *